United States Patent [19]
Naslund

[11] 4,133,339
[45] Jan. 9, 1979

[54] NEEDLE WITH DEFORMABLE EYE

[75] Inventor: Erik I. Naslund, Los Gatos, Calif.

[73] Assignee: Floss Aid Corporation, Santa Clara, Calif.

[21] Appl. No.: 823,594

[22] Filed: Aug. 11, 1977

Related U.S. Application Data

[63] Continuation of Ser. No. 595,078, Jul. 11, 1975, abandoned.

[51] Int. Cl.² ............................................. A61C 15/00
[52] U.S. Cl. ...................... 132/89; 128/339; 223/102
[58] Field of Search ............... 132/89, 93; 223/102; 128/339

[56] References Cited

U.S. PATENT DOCUMENTS

| 741,556 | 10/1903 | Sessums | D3/19 R X |
|---|---|---|---|
| 1,449,068 | 3/1923 | Snyder | 128/339 |
| 1,506,262 | 8/1924 | Slater | 128/339 X |
| 2,931,371 | 4/1960 | Petitta | 132/89 |
| 3,233,800 | 2/1966 | Catania | 223/102 |
| 3,779,256 | 12/1973 | Maloney | 132/93 |
| 3,929,144 | 12/1975 | Tarrson | 132/93 |

Primary Examiner—Russell R. Kinsey
Assistant Examiner—Wenceslao J. Contreras
Attorney, Agent, or Firm—Thomas Schneck, Jr.

[57] ABSTRACT

A needle for leading dental floss or other fibrous material through narrow apertures. A curved substantially rigid needle is provided with an eye having resilient, deformable sides for temporary expansion of the eye for ease of threading and for temporary compression in passing through narrow apertures.

16 Claims, 12 Drawing Figures

NEEDLE WITH DEFORMABLE EYE

This is a continuation of application Ser. No. 595,078, filed July 11, 1975 now abandoned.

FIELD OF THE INVENTION

The invention relates generally to needles and more particularly to needles used as dental appliances in leading dental floss through narrow apertures between teeth, such as under fixed dental bridges, i.e. flossing needles.

PRIOR ART

The idea of using a needle for leading dental floss through apertures between teeth is generally known. FIGS. 1a, 1b, 1c, 1d and 1e illustrate flossing needles which were being sold at the time of the filing of this patent application. The needle of FIG. 1a is a single piece of plastic monofilament which is folded back on itself and fused or bonded for approximately half of the folded length, leaving the unjoined length to form an eye. One of the benefits of this needle is that it is easy to thread, but it suffers the problem of not being rigid and thus difficult to use. To increase its rigidity it becomes necessary to select a monofilament of a larger diameter. However, this will also make the loop more rigid and decrease its ability to collapse as it is passed through a constricted aperture. Further, it would tend to produce a needle with an objectionable thickness dimension.

The needle of FIG. 1b is difficult to thread because of the small eye. Moreover, the hole is surrounded by inflexible walls which appreciably add to the overall width of the needle which, in turn, increases the interference with the soft gum tissue as the needle is passed under a dental bridge.

The needle shown in FIG. 1c is quite easy to thread, but the notch tends to severly weaken the needle and in compensation the width as well as the thickness of the needle must be correspondingly increased. These increased dimensions restrict to a large degree the use of this needle.

FIG. 1d describes a needle design which employs a relatively soft metal wire of a small diameter, commonly used in orthodontic appliances. Besides being marketed as a commercial item by some manufacturers, this type of needle is often made in the dental office by the dentist or his assistant for the patients' use. While this filamentary type of needle may have very small cross sectional dimensions and may incorporate an enlarged, deformable eye for passage through small apertures, it lacks overall rigidity due to the extreme softness of the wire. Furthermore, the wire ends, arising from the filamentary character of the needle, are sharp enough to be capable of injuring gum tissues if the needle is not handled carefully by the user. The wire ends are also objectionable in the needle design described by FIG. 1e where the wire ends are located at the rear end of needle instead of the leading end.

It is an object of the present invention to devise a flossing needle which will be relatively easy to thread, have adequate strength and rigidity but with small enough cross sectional dimensions to permit convenient and painless passage through restricted apertures.

SUMMARY OF THE INVENTION

The above objective is met with a needle, preferably of a plastic material, having a semi-rigid curved forward body portion and a rearward end defining an eye with resilient, deformable sides for temporary expansion of the eye for ease of threading and for temporary compression in passing through narrow apertures. The needle of the present invention is non-filamentary, i.e. unitary, in construction.

The body of the present apparatus has a rigidity at least as great as the rigidity of a similar body made of nylon. At the same time, the material of the body is pliable so that the needle will not break in threading an aperture, such as an aperture existing under a dental bridge.

Moreover, the rearwardmost portion of the eye has a diminished thickness. This diminished thickness of the rearwardmost portion of the eye compensates for the double thickness of floss and allows floss overlap with the eye without causing a bulge which would occur without such a modification. Conversely, the diminished thickness where floss overlaps permits a corresponding increase in the thickness of the forward portion of the needle thereby appreciably adding to the rigidity of the needle.

DESCRIPTION OF THE PREFERRED EMBODIMENT

Figure 1C:
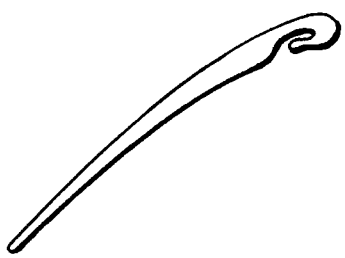
FIGS. 1a, 1b, 1c, 1d and 1e show top views of flossing needles of the prior art.
Figure 1A:
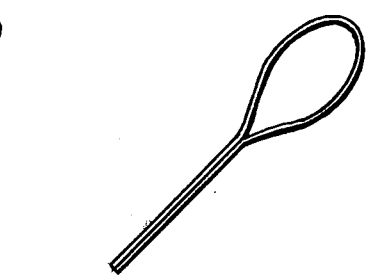
Figure 1B:
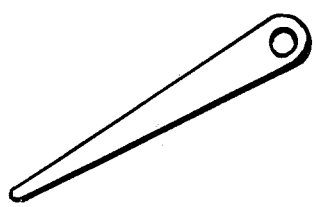
Figure 1D:
Figure 1E:
Figure 2:
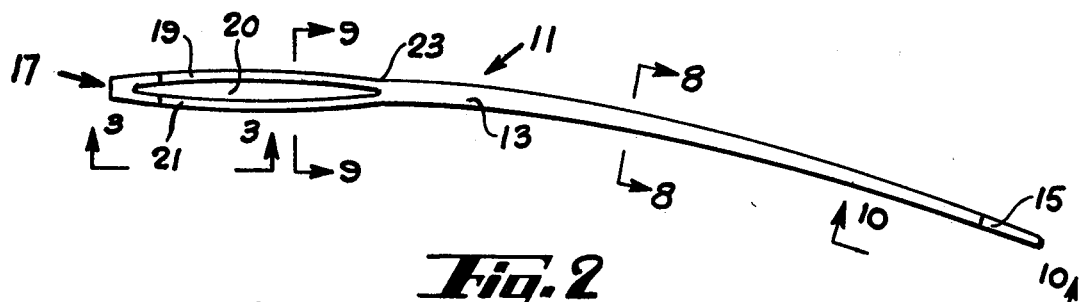
FIG. 2 shows a top view of a first embodiment of the apparatus of the present invention.

In FIG. 2 needle 11 of the present invention is shown to have a unitary structure with a central curved body portion 13, a forward end 15 and a rearward end 17. The rearward end 17 includes resilient, deformable sides 19, 21 which because of their dimensions and the material of which they are made are deformable under light pressure for temporary expansion and compression of the eye. In its relaxed state the eye is large enough for easy threading and it can be pried open further if desired. For instance, if pressure is applied in the direction of the arrow, next to numeral 17, the width of the eye 20, formed by sidewall members 19, 21 will increase to allow easier entry of floss into the eye. Similarly, when needle 11 passes through a narrow aperture, as between teeth, the deformable sides 19, 21 will compress to allow the needle to more easily pass through the aperture.

The body portion 13 of needle 11 has a maximum width near region 23 selected to be approximately 0.040 inches. This width gives good rigidity to the curved needle body 13.

The width of sidewalls 19, 21 is generally uniform along the length of the eye and is approximately 0.016 inches in width for each wall. This dimension is selected such that the combined width of sidewalls 19, 21 is less than the maximum body width (0.016 + 0.016 < 0.040 inches). In any event, the combined maximum width of the deformable sidewalls is less than twice the maximum width of the needle body apart from the needle eye. The width of the relaxed eye between the inside walls of the sidewalls 19, 21 is approximately 0.040 inches.

The ability of the present needle to successfully lead floss through narrow apertures between teeth, under bridgework and the like, is partially due to the ability of the width of the eye to compressibly deform. Since the compressed thickness of dental floss is typically 0.002 to 0.004 inches, that dimension, when added to the width of the two walls does not exceed the maximum body width at region 23 of needle 11.

The term "width" refers to the transverse distance across wall 19, 21 and the body portion 13 of needle 11. The width dimension is parallel to the plane of the paper in FIG. 2.

Figure 3:
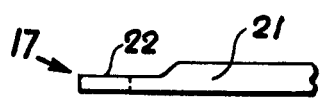
FIG. 3 shows a side sectional view taken along the lines 3—3 of FIG. 2.
Figure 8:
FIG. 8 is a sectional view taken along the lines 8—8 of FIG. 2.
Figure 9:
FIG. 9 is a sectional view taken along the lines 9—9 of FIG. 2.

FIG. 3 is a sectional view of a portion of the apparatus of FIG. 2 and illustrates the thickness of sidewalls 19 and 21 in FIG. 2. The term "thickness" refers to the dimension of needle 11 into the plane of the paper in FIG. 2, i.e. perpendicular to the width. In FIG. 3, the rearwardmost portion of sidewall 19, and also of sidewall 21, has a diminished thickness near region 17, resembling a step. The length of the diminished thickness is approximately 0.093 inches and the diminished thickness itself is approximately 0.013 inches, compared to the regular thickness of the needle of approximately 0.017 inches. The diminished rearward thickness of needle 11, as illustrated in FIG. 3, is intended to compensate for the double compressed thickness of the floss when floss is threaded through the eye and folded over the end of the needle. Thus the reduction in thickness should equal twice the compressed thickness of the floss. At the same time, the lateral dimension of the needle, or the width is compressed as it passes through a restricted aperture due to the temporary deformation of the walls thereby allowing the rearward portion of the needle to become constricted about the floss with the total dimension of the eye with floss in place comparable to the maximum width and thickness of the main body portion of the needle.

The body portion of the needle describes a gentle curve with a radius of curvature for the portion from the maximum body width, 23 in FIG. 1 to the forward tip 15 being equal to approximately 1¾ inches. This curvature allows needle 11 to curve away from the tongue or the walls of the mouth cavity so that it can be gripped more easily for completion of the passage through the aperture.

Figure 10:
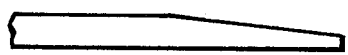
FIG. 10 is a side view taken along the lines 10—10 of FIG. 10.

The radius of curvature of the inside walls 19, 21 at each end of the elongated eye is approximately 0.004 inches, while the radius of the rounded forward end 15 is approximately 0.016 inches. The rounded forward end of needle 11 reduces the possibility of injury or the sensation of pain if gum tissue is accidentally pricked by the needle. The thickness of the needle 11 tapers down to approximately 0.010 inches at the forwardmost end 15 of the needle, thereby providing a slight taper which eases entry of the needle into narrow apertures, as seen in the sectional view of FIG. 10. Similarly, the slight taper in width of the needle from region 23 and forward assists in guiding the needle through apertures.

The needle illustrated in FIGS. 2, 3, 8, 9 and 10 is preferably injection molded of a material which yields a semi-rigid needle, i.e. a needle which has good rigidity, but is not brittle. The rigidity of the present needle is at least equal to a similar needle which is made of nylon and has good tensile strength properties, i.e. comparable to nylon. Brittleness must be avoided since breakage of the needle could be harmful. For this reason plastics such as polystyrene should be avoided. A suitable material for the present invention having good molding characteristics, which yields a needle with good rigidity, yet which is not brittle is acetal copolymer plastic. This material is manufactured by Celanese Plastics Company under the tradename of Celcon M-270. By injection molding needles of the present invention, a clean, precise geometry may be achieved. Moreover, the injection molding process is economical for large scale production of the needle.

Figure 11:
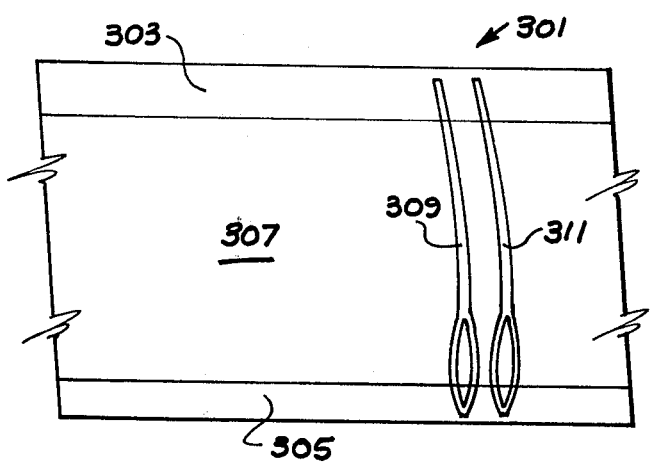
FIG. 11 is a plan view of a construction of the apparatus of the present invention from extruded plastic strip material.

With reference to FIG. 11, the needle of the present invention can also be made through a stamping process in which the needles are punched out of strip stock of a plastic material having good tensile strength properties and good rigidity, at least as good as nylon or preferably Delrin, the latter material being a tradename for an acetal homopolymer plastic manufactured by DuPont deNemours & Co. A practical method of achieving the rearward step described previously with reference to FIG. 3 and the forward taper described with reference to FIG. 10 would be achieved by using an extruded strip with a cross section which already incorporates the taper as well as the step. For example, FIG. 11 shows an extruded strip 301, having one edge 303 with a forward taper and another edge 305 with a rearward step. The central portion 307 between edges 303 and 305 is flat. Needles 309, 311 are punched from strip 301 and are shown as they would appear after punching if placed in the position from whence they came.

Figure 12:
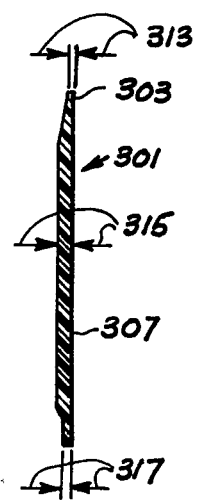
FIG. 12 is a side sectional view of the extruded plastic strip of FIG. 11.

FIG. 12 shows a side view of strip 301 corresponding to FIG. 11. The thickness of strip 301 at the narrowest portion of the tapered edge 303 is 0.010 inches, indicated between arrows 313. The thickness of central portion 307 is 0.017 inches, indicated between arrows 315. The thickness of strip 301 at the narrowest portion of the step edge 305 is 0.013 inches, indicated between arrows 317.

Figure 4:
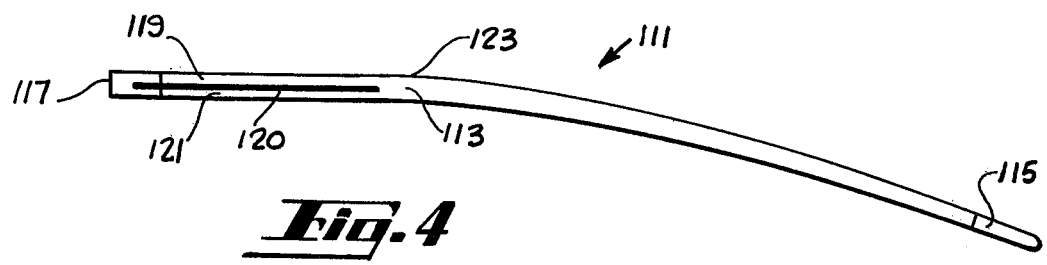
FIG. 4 shows a top view of a first alternate embodiment of the apparatus of the present invention.

FIG. 4 illustrates an alternate needle 111 which is not molded, but stamped, having an eye with deformable walls with the difference, however, that its walls are deformable in a plane which is at right angles to the surface of the needle body. The alternate embodiment of FIG. 4 shows a needle 111 having a body 113, with a rearward end 117 and a forward end 115. An eye, 120, having zero width, is formed during the stamping operation in the rearward portion 117 of the body through a shearing action of the die. Simultaneously the eye is permanently opened by the die by stretching one sidewall 119 in FIG. 5 to assume the desired shape.

Maximum width of needle 111 is at the region of the body indicated at 123. The overall width across the eye 120 is approximately equal to or slightly less than the maximum body width at region 123. Expanded sidewall 119 is deformable and resilient, and provides a large opening for easy threading of the floss.

Body 113 has a diminished thickness at 122 formed by a step in the thickness of the body material at the rearwardmost portion of the body. The step 122 allows floss to be folded over the rearward portion 117 of needle 111 and minimizes the bulge produced by the overlap of floss over the rearward portion of the needle.

Figure 5:
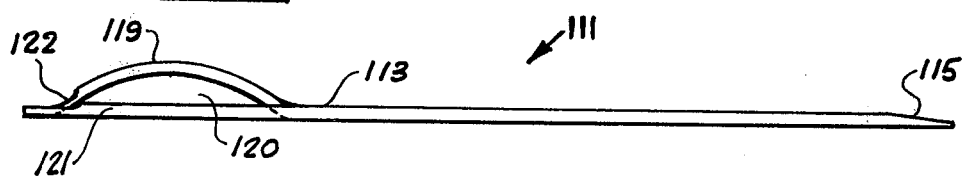
FIG. 5 shows a side view of the apparatus of FIG. 4.

The needle of FIG. 5 has a tapered forward end 115 to ease the entry into a passageway and a rounded point to minimize the risk of puncturing gum tissue. Needle 111 also has a gradual curvature over the entire length of the body 113 to curve away from the walls of the mouth cavity when the needle passes through apertures between teeth.

Figure 6:
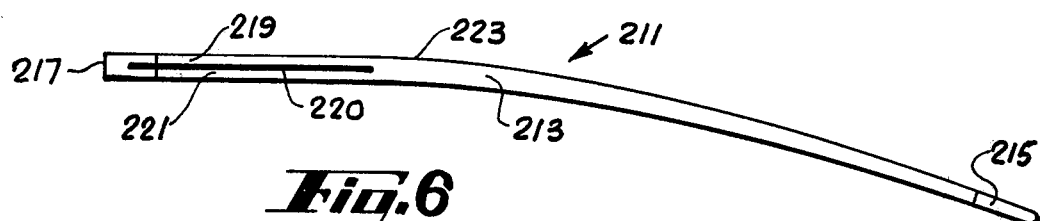
FIG. 6 shows a top view of a second alternate embodiment of the apparatus of the present invention.
Figure 7:
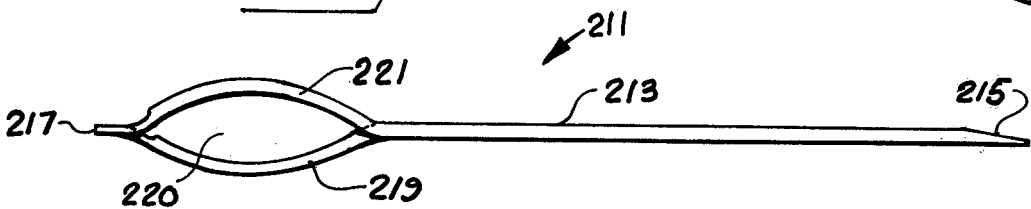
FIG. 7 shows a side view of the apparatus of FIG. 6.

FIG. 6 illustrates a second alternate embodiment which like the embodiment of FIG. 4, has a zero width eye, but unlike the embodiment of FIG. 4, is formed by injection molding. The dimensions of the needle of FIG. 6 generally follow the dimensions of the needle of FIG. 4 except for the eye 220 and the sidewalls 219, 221 on either side of the eye 220. In the side view of FIG. 7, one sidewall, 219 is seen to be raised, while the opposite sidewall 221 is seen to be lowered, i.e. at least one sidewall projects outside of the plane defined by the needle body. The sidewalls may be compressed so that the thickness of the eye of FIG. 7 is reduced to substantially the same thickness as that of the body. The rearwardmost portion 217 of body 213 comprises a step for overlap of floss with the rearwardmost portion of a body 213. Body 213, as seen in FIG. 6, again has a rounded forward end and a gentle suture-like curvature for curving away from mouth cavity walls when in use. It also has a slightly tapered thickness at forward end which can be seen in FIG. 7. While the needle eye of FIG. 6 has zero width, it has a thickness which is compressible approximately to the maximum body thickness.

The above mentioned step 122 and the forward taper 115 can be achieved by stamping the needle from an extruded strip as described with reference to FIG. 11.

In each of the alternate embodiments, the material used for construction of the flossing needle of the present invention is a semi-rigid, non-brittle plastic such as acetal copolymer (Celcon) or acetal homopolymer (Delrin) and the rigidity is at least as rigid as a comparable nylon needle would be.

In summary, a flossing needle has been disclosed which has a one piece construction, i.e. has a unitary body, and has a semi-rigid, curved, forward component with rounded and tapered forward end, the rearward end defining an eye with resilient, deformable sides. The sides may be temporarily deformed for expansion of the eye for easier threading and for compression of the eye for easier passage through an aperture. A high degree of rigidity may be achieved by selecting materials whose rigidity is at least equal to that of nylon. The needle of the present invention is easy to thread, yet avoids bulges at the eye by a diminished thickness at the rearwardmost portion of the eye.

I claim:

1. A needle for leading dental floss and the like through narrow apertures comprising,
    a semi-rigid needle body having a rearward end defining an elongated eye between opposed resilient, deformable sides for temporary expansion and compression of the eye, said eye having a fixed forward and rearward radius between said opposed deformable sides, the combined maximum width of both of said deformable sides is less than twice the maximum width of the needle body apart from said eye.
2. The apparatus of claim 1 wherein the rearwardmost portion of said eye has a diminished thickness.
3. The apparatus of claim 1 wherein said body is curved.
4. The apparatus of claim 1 wherein said semi-rigid body has the rigidity of acetal polymeric plastic.
5. The apparatus of claim 1 wherein said needle body has a forward portion whose thickness is tapered.
6. The apparatus of claim 1 wherein said needle body has a forward portion with a forward rounded end.
7. The apparatus of claim 1 wherein each radius of curvature where said opposed deformable sides of said eye are joined is between 0.001 inches and 0.020 inches.
8. The apparatus of claim 1 wherein a needle body portion extends rearward of said eye for reinforcing said eye.
9. A needle for leading dental floss and the like through narrow apertures comprising,
    a semi-rigid needle body having a pre-selected maximum body width, said body having a rearward end defining an eye between opposed, resilient deformable sides for temporary expansion and compression of the eye, said opposed deformable sides having thickness and width dimensions, the combined coplanar width of the two sides being less than the maximum body width of said needle.
10. The apparatus of claim 9 wherein said needle body has a forward portion whose thickness is tapered.
11. The apparatus of claim 9 wherein said needle body has a forward portion with a forward rounded end.
12. The apparatus of claim 9 wherein a needle body portion extends rearward of said eye for reinforcing said eye, said portion and the rearwardmost portion of said eye having a diminished thickness.
13. The apparatus of claim 9 wherein said deformable sides of said eye are joined at each end, the rearward end of the eye defining a radius.
14. The apparatus of claim 13 wherein each radius of curvature where said opposed deformable sides of said eye are joined is between 0.001 inches and 0.020 inches.
15. The apparatus of claim 1 wherein said needle is made of acetal copolymer plastic.
16. The apparatus of claim 1 wherein the combined maximum width of both of said deformable sides is less than 0.080 inches.